United States Patent
Tanaka et al.

(10) Patent No.: US 7,183,421 B2
(45) Date of Patent: Feb. 27, 2007

(54) PROCESSES FOR PRODUCING OXIDE WITH HIGHER OXIDATION THAN ALCOHOL

(75) Inventors: Hideo Tanaka, Okayama (JP); Yutaka Kameyama, Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 10/915,600

(22) Filed: Aug. 11, 2004

(65) Prior Publication Data

US 2005/0014957 A1    Jan. 20, 2005

Related U.S. Application Data

(62) Division of application No. 09/959,844, filed as application No. PCT/JP01/01838 on Mar. 9, 2001, now Pat. No. 6,797,830.

(30) Foreign Application Priority Data

Mar. 9, 2000    (JP)  ............................. 2000-064720

(51) Int. Cl.
*C07D 309/00* (2006.01)
*C07D 407/00* (2006.01)
*C07C 67/00* (2006.01)
*C07C 51/16* (2006.01)
*C07C 45/00* (2006.01)

(52) U.S. Cl. ................. 549/273; 549/295; 549/307; 560/239; 562/409; 568/322; 568/426; 568/485

(58) Field of Classification Search ............... 549/273, 549/295, 307; 560/239; 562/409; 568/322, 568/426, 485

See application file for complete search history.

(56) References Cited

FOREIGN PATENT DOCUMENTS

| JP | 05-02507 | 2/1993 |
| JP | 06-211827 | 8/1994 |

OTHER PUBLICATIONS

Inokuchi et al., Indirect Electrooxidation of Alcohols by a double Mediatory System, J. Org. Chem. vol. 56 pp. 2416-2421 (1991).*
Bobbitt et al, J. Org. Chem. vol. 63 pp. 9367-9374 (1998).*
Inokuchi, T. et al.; "Indirect Electrooxidation of Alcohols by a Double Mediatory System with Two Redox Couples of $[R_2N^4=O]$/$R_2NO$ and $\{Br\text{ or }Br^+\}/Br$ in an Organic-Aqueous Two-Phase Solution"; *J. Org. Chem*; vol. 56, pp. 2146-2421; 1991.
Bobbitt et al., J. Org. Chem, vol. 63, pp. 9367-9374 (1998).

* cited by examiner

*Primary Examiner*—Thomas McKenzie
*Assistant Examiner*—Raymond Covington
(74) *Attorney, Agent, or Firm*—Kubovcik & Kubovcik

(57) ABSTRACT

The present invention provides a process for producing an oxide from an alcohol compound, the process comprising the steps of causing silica gel to carry the alcohol compound thereon and an oxidative catalyst thereon, and oxidizing the alcohol compound in the presence of an oxidizing agent, giving an oxide higher in oxidizing degree than the alcohol compound, and also provides a process for producing an oxide from an alcohol compound, the process comprising the steps of causing silica gel to carry the alcohol compound, and subjecting the alcohol compound to an electrolytic oxidation, giving an oxide higher in oxidizing degree than the alcohol compound.

10 Claims, No Drawings ized oxidation reactions of alcohols using N-oxyl catalyst have been conducted in an organic solvent
PROCESSES FOR PRODUCING OXIDE WITH HIGHER OXIDATION THAN ALCOHOL This application is a division of application Ser. No. 09/959,844, filed Nov. 28, 2001 now U.S. Pat. No. 6,797,830, which is a 371 of PCT/JP01/01838 filed Mar. 9, 2001.

TECHNICAL FIELD

The present invention relates to a process for oxidation of an alcohol compound and more particularly to a process for preparing an oxide higher in oxidizing degree than the alcohol compound by oxidizing the alcohol compound which is sparingly soluble in water.

BACKGROUND ART

The present invention relates to a process for oxidation of alcohol. According to the process of the invention, various organic compounds such as aldehyde compound, ketone compound, lactone compound or the like can be prepared by oxidation of alcohol with high efficiency in a high yield.

In general, the oxidation reaction of alcohol compound is widely utilized in the field of organic synthesis so that numerous processes have been developed.

Especially oxidation reactions using an oxidative catalyst are various and are conducted as useful methods for conversion of functional group which are utilized for numerous types of organic synthesis. Among them, methods using N-oxyl compound as an oxidative catalyst are excellent for selective conversion of functional group in an alcohol and are used in various kinds of oxidation reaction of alcohols.

Conventionally oxidation reactions of alcohols using N-oxyl catalyst have been conducted in an organic solvent or a water-containing organic solvent (Journal by Organic Synthesis Association, published in 1993, vol. 51, pp. 48 to 58, J. Organic Chemistry, 1989, 54, 2970 to 2972, Tetrahedron Letters, 1990, 31, 2177 to 2180, etc.). However, these methods essentially use large amounts of harmful organic solvents such as methylene chloride, so that the methods are undesirable from the viewpoint of preservation of the environment, and are unable to give the contemplated product in fully satisfactory yields.

Also known are methods comprising oxidizing an alcohol in a mixture of water and organic solvent in the presence of N-oxyl compound using hypohalogenous acid salt such as hypochlorite, hypobromite or the like (JP-A-25078/1993, JP-A-211827/1994, etc.). However, the methods also essentially employ an organic solvent and remain to be radically improved for preservation of the environment. Further, when these methods employ sodium hypochlorite and like hypohalogenous acid salt which are low in solubility in an organic solvent, it is difficult to bring about oxidation reaction depending on the kind of alcohol used as the raw material, and the desired product may be produced in a reduced yield. An example of this defect is illustrated in Reference Example 1.

An electrolytic oxidation reaction is electrochemically performed and therefore has drawn attention as a clean oxidation reaction so that some of such reactions are carried out on an industrial scale.

Generally conventional electrolytic alcohol oxidation reaction methods include a direct electrolytic oxidation method to be effected in an organic solvent or a water-containing organic solvent as described in "Electrolytic Organic Synthesis" (Sigeru TORII, published by Kodansha Publishing Co., 1981, pp. 262 to 273), an indirect electrolytic oxidation method using a mediator (electron carrier), and electrolytic oxidation method involving the use of 2-layer system (2 layers each containing water and a water-immiscible organic solvent, respectively) (J. Org. Chem., 1991, 56, 2416 to 2421).

Many reaction systems of these electrolytic oxidation methods use organic solvents which entail difficulty in flow of electric current so that the methods require a large amount of supporting electrolyte, e.g. 10 to 50 wt. % of supporting electrolyte when using N,N-dimethylformamide as a solvent. The large amount of supporting electrolyte used raises a problem of necessitating a cumbersome procedure for isolating and purifying the obtained reaction product as well as problems of high costs and disposal of waste. Also known are methods using various metal catalysts as the mediator. Among them, commercially feasible methods are limited because of serious problems such as high costs of metal compounds and post-treatment.

N-oxyl compound is reportedly superior as a catalyst for electrolytic oxidation reaction of alcohol compound (J. Org. Chem., 1991, 56, 2416 to 2421). Any reactions disclosed in this document, however, are of two-layer system type (methylene chloride/water) and can not be used these days because it is difficult to industrially use methylene chloride for the environmental problem.

As described above, the oxidation reaction of alcohol compound still entails various problems to be overcome or mitigated. Therefore there is a need for development of oxidation reaction which is industrially practical.

An object of the present invention is to provide a novel process for oxidizing an alcohol, the process being capable of giving the contemplated product in a high yield by a simplified reaction operation irrespectively of the type of alcohol used as the raw material without a need to use an organic solvent which is likely to adversely affect the environment, the process being applicable to all kinds of industrial manufacture.

Another object of the invention is to provide a general-purpose process for oxidizing an alcohol, the process comprising subjecting an alcohol compound which is sparingly soluble in water to an electrolytic oxidation in water, the process being free from the drawbacks of conventional electrolytic oxidation processes and capable of producing an oxide which is higher in oxidizing degree than the alcohol as the raw material with high efficiency in a high yield.

DISCLOSURE OF THE INVENTION

The present invention provides a process for producing an oxide from an alcohol compound, the process comprising the steps of causing silica gel to carry the alcohol compound thereon and an oxidative catalyst thereon, and oxidizing the alcohol compound in the presence of an oxidizing agent, giving an oxide higher in oxidizing degree than the alcohol compound.

The present invention also provides a process for producing an oxide from an alcohol compound, the process comprising the steps of causing silica gel to carry the alcohol compound, and subjecting the alcohol compound to an electrolytic oxidation, giving an oxide higher in oxidizing degree than the alcohol compound.

Examples of oxides higher in oxidizing degree than the alcohol are aldehyde, ketone, lactone, carboxylic acid ester, carboxylic acid compound, etc.

According to the inventor's research, the following was found. Since the silica gel carrying N-oxyl compound and alcohol is used in combination with the oxidizing agent, the oxidation reaction of alcohol proceeds on the silica gel so that the alcohol can be efficiently oxidized in the water-containing system without use of an organic solvent. Another finding is that since the reaction is carried out in the water-containing system, the oxidizing agent effectively acts so that the oxidation reaction proceeds with high efficiency irrespectively of the kind of alcohol. The advantage is that since the reaction product and the oxidative catalyst alone are carried on silica gel in the final stage of the reaction, the silica gel is separated by filtration from the aqueous solution after completion of the reaction, and the reaction product and the catalyst can be recovered only by washing the silica gel with a small amount of organic solvent.

Consequently the process for the oxidation of alcohol according to the present invention can produce the desired product by a simple reaction operation irrespectively of the kind of the alcohol used as the starting material in a high yield without a need to use an organic solvent which is likely to adversely affect the environment, the process being applicable to all kinds of industrial manufacture.

According to the inventor's research, the following novel finding was achieved. When the alcohol compound which is sparingly soluble in water, i.e. the starting compound is carried on silica gel, an electrolytic oxidation of alcohol compound proceeds in water, giving the contemplated oxide higher in oxidizing degree than the alcohol by a simplified operation in a high yield.

In accordance with the present invention, the alcohol compound which is sparingly soluble in water can be electrolytically oxidized in an aqueous solution which allows the smooth flow of current without use of an organic solvent, so that the amount of supporting electrolyte to be used can be reduced and the water containing the supporting electrolyte (i.e. an aqueous solution of supporting electrolyte) can be recovered for reuse.

The reaction product and silica gel alone are eventually supported on silica gel after electrolytic oxidation. The process of the invention gives an advantage that the reaction product and catalyst can be recovered only by separating silica gel by filtration and washing the silica gel with a small amount of an organic solvent.

The oxidation method using an oxidizer according to the present invention can be usually effected by adding to a solvent (water) an inorganic oxidizer and silica gel carrying an alcohol and N-oxyl compound thereon.

The electrolytic oxidation method of the invention is performed by causing silica gel to carry an alcohol compound which is sparingly soluble in water, i.e. the starting compound, and placing the silica gel carrying the same into water containing a supporting electrolyte to electrolytically oxidize the alcohol in the conventional manner.

The term "an alcohol compound which is sparingly soluble in water" used herein refers to an alcohol compound which can be carried by silica gel and which has a hydrophobic degree of being scarcely dissolved out in water.

Since the alcohol compound is laid on silica gel in different degrees depending on the kind of the compound, substituent thereof and silica gel, the compound can not be definitely determined according to the solubility of compound in water, molecular weight and the like. Generally an alcohol compound can be employed if sparingly soluble in water. As a matter of fact, if methanol, ethanol, ethylene glycol or like alcohol compounds with a high solubility in water are used, a reaction does not proceed. Accordingly no limitation is imposed on alcohol compounds and a variety of compounds can be used insofar as the compound can be used for oxidation reaction as a rule and can be supported by silica gel.

Examples of alcohol compounds to be used are n-butyl alcohol, n-pentyl alcohol, 2-chloro-n-pentyl alcohol, 3-acetoxy-n-pentyl alcohol, 2-butyl alcohol, 2-pentyl alcohol, 2-phenyl-1-ethanol, 1-phenyl-1-ethanol and like alkyl alcohols, benzyl alcohols and like aralkyl alcohols optionally having a substituent, cyclohexyl alcohols, cyclopentyl alcohols, 4-methoxycyclohexyl alcohols and like cyclo alcohols optionally having a substituent, butanediol, pentanediol, hexanediol, heptanediol, 3-methylhexanediol, 3-acetoxypentanediol; 3-choro-2-methylhexanediol and like alkyl diols, cyclohexane-1,2-diethanol and like cyclodiols, etc. Further examples are triols and compounds having 4 or more hydroxyl groups which can be used without a problem if they can be carried by silica gel. These alcohols may optionally have at least one of the following atoms or groups substituted: halogen, nitro, cyano, aryl, lower alkyl, amino, mono-lower alkylamino, di-lower alkylamino, mercapto, lower alkylthio, arylthio, formyloxy, acyloxy represented by RCOO— (wherein R is lower alkyl or aryl), formyl, acyl represented by RCO— (wherein R is as defined above), lower alkyloxy, aryloxy, carboxyl, lower alkyloxy carbonyl and aryloxy carbonyl. Examples of lower alkyl are alkyl having 1 to 6 carbon atoms, and examples of aryl are phenyl, tolyl, xylyl, naphthyl and the like. Among these alcohols, alkyl alcohols and alkyl diols are preferred, and alkyl alcohols and alkyl diols having 4 or more carbon atoms are more preferred.

The oxide higher in oxidizing degree than alcohol used as the raw material in this invention includes, for example, n-butanal or n-butanoic acid n-butyl ester when n-butyl alcohol is used as the raw material; acetophenone when 1-phenylethanol is used as the raw material; tetrahydro-2-furanone when 1,4-butanediol is used as the raw material; and 8-oxabicyclo[4.3.0]nonane-7-one when 1,2-bis(hydroxymethyl)cyclo-hexane is used as the raw material.

When, for example, N-oxyl compound is used as the oxidative catalyst in the present invention, the desired product can be obtained in a higher yield and the electrical efficiency is increased in the case of electrolytic oxidation. Thus, the N-oxyl compound is preferred. Various kinds of N-oxyl compounds can be used. In view of ease in availability and in modification of functional group, the following N-oxyl compounds are preferred: 4-benzoyloxy-2,2,6,6-tetramethylpiperidine-N-oxyl, 4-(4-tert-butylbenzoyloxy)-2,2,6,6-tetramethylpiperidine-N-oxyl, 4-cyano-2,2,6,6-tetramethylpiperidine-N-oxyl, 4-methoxy-2,2,6,6-tetramethylpiperidine-N-oxyl, 4-hydroxy-2,2,6,6-tetramethylpiperidine-N-oxyl, 2,2,6,6-tetramethylpiperidine-N-oxyl and like piperidine-N-oxyl compounds, 3-benzoyloxymethyl-2,2,5,5-tetramethylpyyrolidine-N-oxyl, 3-methoxycarbonyl-2,2,5,5-tetramethylpyyrolidine-N-oxyl and like pyrrolidine-N-oxyl compounds, di(2,2,6,6-tetramethylpiperidine-N-oyl)-4-yl-1,10-decanoic acid diester and like N-oxyl polymolecule-bonded compounds, (S)-(−)-3,3,5,5-tetramethyl-4H-dinaphtho[2,1-c:1',2'-e]-azepin-N-oxyl and like optically active N-oxyl compounds, etc. The amount of the oxidative catalyst to be used can be properly selected from a wide range according to reaction conditions and the like. The catalyst is used in an amount of usually 0.001 to 25 mole %, preferably 0.2 to 10 mole %, based on the alcohol compound which is sparingly soluble in water. The oxidative catalyst is preferably carried on silica gel together with the alcohol compound. Since the reductant in the oxidation reaction system can be easily converted into an oxidative catalyst, the corresponding reductant can be used.

For example, when the corresponding N-hydroxy compound is used as the oxidative catalyst instead of the N-oxyl compound, the N-oxyl compound which is readily produced in the reaction system can be used in the reaction of the invention. Oxidative catalysts can be used either alone or in combination.

Silica gels to be used in the invention are not limited and can be any of known silica gels and commercially available silica gels. Various shapes of silica gels are known. Yet no limitation is imposed on the shape of silica gels. The amount of the silica gel to be used is not limited and can be properly selected from a wide range according to reaction conditions and the like. It is used in an amount of usually about 0.3 to about 50 kg, preferably about 0.5 to about 5 kg, per kilogram of the compound serving as the raw material.

The alcohol compound as the raw material and the oxidative catalyst are carried on silica gel by being usually dissolved in a suitable organic solvent to obtain a uniform solution, adding silica gel to the solution, thoroughly stirring the mixture and distilling off the organic solvent under reduced pressure. The organic solvent to be used in this operation is one which can dissolve the alcohol and the catalyst and which can be distilled off under reduced pressure. Useful organic solvents include, for example, methanol, ethanol, propanol, isopropanol and like straight chain or branched chain lower alcohols, acetone, methyl isobutyl ketone and like ketones, n-pentane, n-hexane and like straight chain or branched chain lower saturated hydrocarbons, 2-pentene, 1-hexene and like straight chain or branched chain unsaturated hydrocarbons, benzene, toluene and like aromatic hydrocarbons, methylene chloride, chloroform and like halogenated hydrocarbons, ethyl acetate, butyl acetate, dimethyl carbonate and like esters, diethyl ether, diisopropyl ether and like straight chain or branched chain lower alkyl ethers, tetrahydrofuran, dioxane, dioxolan and like cyclic ethers, etc. These solvents are preferably those having a boiling point of lower than 150° C. because the solvent needs to be distilled off under reduced pressure. The amount of the solvent to be used is not limited insofar as the amount is sufficient to dissolve the alcohol compound and electrolytically oxidative catalyst and to cause silica gel to uniformly carry them. The amount of the solvent to be used is small from a viewpoint of industrial scale and is far from imposing a load on the environment and the like.

The oxidation of alcohol using an oxidizer in the invention is usually conducted as described above by adding silica gel carrying the alcohol and N-oxyl compound and an inorganic oxidizer to water as the solvent.

Water is used as the reaction solvent. The amount of water to be used can be properly selected from a wide range depending on the types and amounts of alcohol and N-oxyl compound used, the amount of silica gel used and the like. The amount of water to be used is usually about 2 to about 2000 liters, preferably about 5 to about 100 liters, per kilogram of alcohol. While water in a neutrality range can be used as it is, the reaction may be performed using water adjusted to an alkalinity range by adding a proper alkali material. Useful alkali materials are not limited insofar as an aqueous solution of the alkali material shows alkalinity. Examples are lithium carbonate, sodium carbonate, potassium carbonate and like alkali metal carbonates, beryllium carbonate, magnesium carbonate, calcium carbonate and like alkaline earth metal carbonates, lithium hydrogencarbonate, sodium hydrogencarbonate, potassium hydrogencarbonate and like alkali metal hydrogencarbonates, lithium hydroxide, sodium hydroxide, potassium hydroxide and like alkali metal hydroxides, magnesium hydroxide, calcium hydroxide and like alkaline earth metal hydroxides and like alkaline inorganic salts, etc. These alkali materials can be used either alone or in combination. The amount of the alkali material to be used is not limited and is 0.01 wt. % to saturated amount, preferably 0.1 wt. % to saturated amount.

An organic solvent which is miscible with water can be added within the range which does not adversely affect the reaction. Useful organic solvents are, for example, methanol, ethanol, n-propanol, iso-propanol and like lower alkyl alcohols, tetrahydrofuran, dioxane, dioxolan and like cyclic ethers, dimethylformamide, diethylformamide, dimethylacetamide and like amides, N-methylpyrrolidinone and like cyclic amides, dimethylsulfoxide, etc. The amount of the organic solvent to be used is properly selected according to the kind of the organic solvent, kind, shape and amount of silica gel, etc. Usually 30 wt. % or less of the total amount of water and organic solvent is used.

There is no limitation on the oxidizing agent to be used herein. Useful oxidizers include any of known compounds which can oxidize the reductant of N-oxyl compound. In view of the solubility of water as the solvent adjusted to an alkalinity range and the reaction rate, for example, the following compounds can be used: lithium hypochlorite, sodium hypochlorite, potassium hypochlorite, lithium hypobromite, sodium hypobromite, potassium hypobromite, lithium hypoiodite, sodium hypoiodite, potassium hypoiodite and like alkali metal salts of hypohalogenous acid, calcium hypochlorite, calcium hypobromite, calcium hypoiodite and like alkaline earth metal salts of hypohalogenous acid, lithium chlorite, sodium chlorite, potassium chlorite, lithium bromite, sodium bromite, potassium bromite, and like alkali metal salts of halogenoic acid, calcium chlorite, calcium bromite, calcium iodite and like alkaline earth metal salts of halogenoic acid, lithium chlorate, sodium chlorate, potassium chlorate, lithium bromate, sodium bromate, potassium bromate, lithium iodate, sodium iodate, potassium iodate and like alkali metal salts of halogenoic acid, calcium chlorate, calcium bromate, calcium iodate and like alkaline earth metal salts of halogenoic acid, molecules of halogen such as chlorine, bromine, iodine and the like, combinations of hydrogen peroxide, sodium peroxide, potassium peroxide or like hydrogen peroxide derivatives with tungstic acid, sodium tungstate or like metal oxidative catalysts, performic acid, peracetic acid, m-chloroperbenzoic acid and like carboxylic acid peroxides, molecular oxygen, oxidation-activators comprising molecular oxygen and metal catalyst, etc. Examples of metal catalysts to be combined with molecular oxygen can be any of known compounds such as cupric chloride, cupric bromide, cupric iodide and like cupric halides, ruthenium chloride, ruthenium oxide, ruthenium chloride triphenyl phosphine complexes and like ruthenium catalysts, and the above-mentioned compounds produced in a reaction system using other compounds. The oxidizing agents can be used either alone or in combination. The amount of the oxidizing agent to be used is less than 20 moles, preferably 1 to 10 moles, per mole of the alcohol although properly selectable from a wide range according to the reaction product, reaction conditions, etc.

A halogen-containing salt may be added to the reaction system to achieve the oxidation reaction with a higher efficiency in the present invention. Useful halogen-containing salts include conventional compounds such as lithium chloride, sodium chloride, potassium chloride, lithium bromide, sodium bromide, potassium bromide, lithium iodide, sodium iodide, potassium iodide and like halogenated alkali metal salts, beryllium chloride, magnesium chloride, calcium chloride, beryllium bromide, magnesium bromide, calcium bromide, beryllium iodide, magnesium iodide, calcium iodide and like halogenated alkaline earth metal salts, ammonium chloride, ammonium bromide, ammonium iodide and like halogenated ammonium salts, tetramethylammonium chloride, tetramethylammonium bromide, tetramethylammonium iodide, tetraethylammonium chloride, tetraethylammonium bromide, tetraethylammonium iodide, tetrabutylammonium chloride, tetrabutylammonium bromide, tetrabutylammonium iodide, and like halogenated tetraalkylammonium and the like. These halogen-containing salts can be used either alone or in combination. The amount of the halogen-containing salt to be used is about 0.01 to about 50 wt. %, preferably about 0.1 to about 25 wt. %, based on the amount of water used.

The reaction of the invention is carried out at a temperature in the range of about −5 to about 100° C., preferably 0 to about 60° C., and is completed in about 5 minutes to about 20 hours, preferably about 10 minutes to about 5 hours.

The electrolytic oxidation method of the invention is performed as described above by causing silica gel to support thereon the alcohol compound as the raw material which is sparingly soluble in water, adding the compound carried on the carrier to water containing a supporting electrolyte and subjecting the same to electrolytic oxidation in the conventional manner. Namely the alcohol compound supported on the silica gel is electrolytically oxidized in the presence of the supporting electrolyte.

Useful supporting electrolytes can be any of salts which are soluble in water and which allows the flow of electric current. Examples are halogenated alkali metal salts, halogenated alkaline earth metal salts, alkali metal carbonate, alkaline earth metal carbonate, alkali metal hydrogencarbonate, alkali metal phosphate, alkaline earth metal phosphate, halogenated ammonium salt, halogenated tetraalkyl ammonium salt, ammonium salt of carbonic acid, ammonium salt of phosphoric acid, tetraalkyl ammonium salt of phosphoric acid, alkali metal sulfate, alkali metal hydrogensulfate, tetraalkyl ammonium hydrogensulfate, alkaline earth metal sulfate, hypochlorite, metal salt of perchloric acid, ammonium salt of perchloric acid, ammonium salt of sulfonic acid, metal salt of borofluoride, ammonium salt of borofluoride, etc.

Specific examples of useful supporting electrolytes are lithium chloride, sodium chloride, potassium chloride, lithium bromide, sodium bromide, potassium bromide, lithium iodide, sodium iodide, potassium iodide and like halogenated alkali metal salts, beryllium chloride, magnesium chloride, calcium chloride, beryllium bromide, magnesium bromide, calcium bromide, beryllium iodide, magnesium iodide, calcium iodide and like halogenated alkaline earth metal salts, lithium carbonate, sodium carbonate, potassium carbonate and like alkali metal carbonates, beryllium carbonate, magnesium carbonate, calcium carbonate and like alkaline earth metal carbonates, lithium hydrogencarbonate, sodium hydrogencarbonate, potassium hydrogencarbonate and like alkali metal hydrogencarbonates, sodium dihydrogenphosphate, disodium phosphate, potassium dihydrogenphosphate, dipotassium phosphate and like alkali metal phosphates, magnesium phosphate, calcium phosphate and like alkaline earth metal phosphates, ammonium chloride, ammonium bromide, ammonium iodide and like halogenated ammonium salts, tetramethylammonium chloride, tetramethylammonium bromide, tetramethylammonium iodide, tetraethylammonium chloride, tetraethylammonium bromide, tetraethylammonium iodide, tetrabutylammonium chloride, tetrabutylammonium bromide, tetrabutylammonium iodide and like halogenated tetraalkylammoniums, ammonium carbonate, ammonium hydrogencarbonate and like ammonium salts of carbonic acid, ammonium dihydrogenphosphate, diammonium phosphate and like ammonium salts of phosphoric acid, tetraethylammonium dihydrogenphosphate, tetrabutylammonium dihydrogenphosphate and like tetraalkylammonium salts of phosphoric acid, lithium sulfate, sodium sulfate, potassium sulfate and like alkali metal sulfates, lithium hydrogensulfate, sodium hydrogensulfate, potassium hydrogensulfate and alkali metal hydrogensulfates, tetraethylammonium hydrogensulfate, tetrabutylammonium hydrogensulfate and like tetraalkylammonium hydrogensulfates, magnesium sulfate, calcium sulfate and like alkaline earth metal sulfates, sodium hypochlorite, potassium hypochlorite, calcium hypochlorite and like hypochlorites, lithium perchlorate, sodium perchlorate, magnesium perchlorate and like metal salts of perchloric acids, ammonium perchlorate, tetraethylammonium perchlorate, tetrabutylammonium perchlorate and like ammonium salts of perchloric acid, tetrabutylammonium tosylate and like ammonium salts of sulfonic acid, lithium borofluoride, sodium borofluoride and like metal salts of borofluoride, tetraethyl ammonium borofluoride, tetrabutylammonium borofluoride, and like ammonium salts of borofluoride. Among them, halogenated alkali metal salts and halogenated alkaline earth metal salts are preferable. These supporting electrolytes can be used either alone or in combination. The amount of the supporting electrolyte to be used is properly selected from a wide range depending on reaction conditions and is such that an aqueous solution of supporting electrolyte has a concentration of about 0.01 to about 70 wt. %, preferably about 0.1 to about 50 wt. %.

The amount of water to be used in the electrolytic reaction of the invention is not limited and can be properly selected according to reaction conditions and the like. It is in the range of about 2 to about 2000 liters, preferably about 5 to about 100 liters, per kilogram of the compound as the raw material. No problem would arise if a proper organic solvent which is miscible with water is mixed with water to an extent that the needed organic substance carried on silica gel does not flow out. Examples of useful solvents which would not raise a problem are tetrahydrofuran, dioxane, dioxolan and like cyclic ethers, dimethylformamide, diethylformamide, dimethylacetamide and like amides, N-methylpyrrolidinone and like cyclic amides, dimethylsulfoxide, etc. The amount of the solvent to be mixed with water is properly selectable depending on the kind, shape and amount of silica gel and the kind of the solvent, and is usually 30 wt. % or less based on the amount of water used.

The electrolytic reaction of the invention is carried out at a temperature of −5 to about 100° C., preferably 0 to about 60° C.

Electrodes to be used in conventional electrolytic reactions can be widely used in the electrolytic oxidation method of the invention. Stated more specifically, useful anode materials are, for example, platinum, stainless steel, nickel, lead oxide, carbon, iron oxide, titanium and the like, and useful cathode materials are, for example, platinum, tin, aluminum, stainless steel, zinc, lead, copper, carbon and the like. Among them, platinum, carbon, stainless steel and the like are preferred as anode materials and platinum, stainless steel, copper, carbon and the like are preferred as cathode materials.

The electrolytic oxidation of the invention can be carried out with the anode and the cathode optionally separated with a diaphragm, namely is characterized in that the oxidation is feasible in a single cell.

The electrolytic reaction of the invention may be conducted by either a constant current electrolytic method or a constant voltage electrolytic method. In view of simplified apparatus or ease of operation, the constant current electrolytic method is preferably conducted. The electrolysis can be conducted with either a direct current or an alternating current, and the current direction may be changed over every one to thirty seconds. The current density is 1 to 200 mA/cm$^2$, preferably 1 to 100 mA/cm$^2$. The quantity of electricity is variable depending on the shape of the electrolytic cell used, the kind of starting material used, the kind of solvent used and the like. It is about 2 to about 20 F/mole, preferably about 2 to about 8 F/mole. The reaction is completed by passage of electricity in the above quantity.

The contemplated product obtained by the reaction of the invention can be easily isolated and purified by separating the silica gel from the reaction system by filtration or otherwise, washing the obtained silica gel with a small amount of an organic solvent such as acetone, concentrating the organic solvent, and subjecting the residue to column chromatography or the like. The silica gel washed with the organic solvent can be reused as an oxidative catalyst.

BEST MODE OF CARRYING OUT THE INVENTION

The present invention will be described in more detail with reference to the following examples to which the invention, however, is not limited.

REFERENCE EXAMPLE 1

Dissolved in 2 ml of methylene chloride were 100 mg (0.64 mmol) of 1-(p-chlorophenyl)ethyl alcohol and 1.9 mg (0.0064 mmol) of 4-benzoyloxy-2,6-tetramethylpiperidine-N-oxyl compound. To the solution was added dropwise 5 ml of an aqueous solution of 3.52 mmol (as the quantity of active chlorine) of sodium hypochlorite at a temperature of 1 to 2° C. After addition, the reaction mixture was separated and the methylene chloride layer was concentrated Purification was conducted by column chromatography, whereby 2 mg (2% yield) of 1-(p-chlorophenyl)ethyl-1-one was given and 95% of 1-(p-chlorophenyl)ethyl alcohol serving as the raw material was recovered.

EXAMPLE 1

Uniformly dissolved in 2 ml of acetone were 157 mg (1.0 mmol) of 1-(p-chlorophenyl)ethyl alcohol and 3.0 mg (0.01 mmol) of 4-benzoyloxy-2,6-tetramethylpiperidine-N-oxyl compound. To the solution was added 1 g of silica gel (product of Merck, grade 9385) and the mixture was vigorously stirred for 5 minutes. Then the acetone was distilled off under reduced pressure. The obtained silica gel was placed into an eggplant type flask, which was immersed in an ice bath and was cooled to 1 to 2° C. A solution of sodium hypochlorite (5 ml of aqueous solution containing 1.1 mmols of active oxygen) which was cooled was added gradually dropwise thereto. After completion of addition, the reaction mixture was stirred at the same temperature for 30 minutes. After completion of agitation, the reaction mixture was filtered, and the silica gel remaining on the filter paper was washed with 5 ml of acetone, whereby the desired product and catalyst were recovered. Acetone was removed by concentration and the residue was purified by silica gel column chromatography, giving 148 mg of 1-(p-chlorophenyl)ethyl-1-one in a yield of 96%. $^1$H-NMR data of obtained ketone product were as follows.

$^1$H-NMR (200 MHz, CDCl$_3$)

δ ppm: 2.60(s, 3H), 7.60(d, J=8.1 Hz, 2H), 7.81(d, J=8.1 Hz, 2H)

EXAMPLE 2

A reaction was carried out in the same manner as in Example 1 except that the amount of hypochlorous acid was changed as follows:

| Amount of hypochlorous acid (mole equivalent) | Yield (%) |
|---|---|
| 1.5 | 95 |
| 3.5 | 94 |
| 5.5 | 92 |

$^1$H-NMR data of obtained product were identical with those of obtained product in Example 1.

EXAMPLE 3

A reaction was performed in the same manner as in Example 1 with the exception of adding the following alkaline salts to the aqueous solution of hypochlorous acid used.

| Alkaline salt | (conc., wt %) | Yield (%) |
|---|---|---|
| NaHCO$_3$ | (3) | 95 |
| NaHCO$_3$ | (saturated) | 95 |
| NaOH | (3) | 93 |
| KOH | (3) | 94 |
| Na$_2$CO$_3$ | (10) | 92 |
| K$_2$CO$_3$ | (10) | 93 |
| KHCO$_3$ | (6) | 95 |
| Ca(OH)$_2$ | (3) | 95 |

H-NMR data of obtained product were identical with those of obtained product in Example 1.

EXAMPLE 4

A reaction was carried out in the same manner as in Example 1 except that the kind of silica gel to be used was changed as follows:

| | |
|---|---|
| Wakogel c-200 | 96% |
| (trade name, product of Wako Pure Chemical Ind., Ltd.) | |
| Wakogel c-300 | 95% |
| (trade name, product of Wako Pure Chemical Ind., Ltd.) | |
| Silica Gel 60 | 94% |
| (spherical, product of Kanto Kagaku K.K.) | |
| Silica Gel 60 | 96% |
| (spherical, neutral, product of Kanto Kagaku K.K.) | |
| Silica Gel 60 | 95% |
| (spherical, 100 to 200 mesh, product of Kanto Kagaku K.K.) | |
| Silica Gel 60 | 93% |
| (spherical, 40 to 100 mesh, product of Kanto Kagaku K.K.) | |
| YMC Gel (SIL-60-230/70, product of YMC K.K.) | 95% |
| Silica Gel 60 (KO70, product of Katayama Gel K.K.) | 92% |

$^1$H-NMR data of obtained product were identical with those of obtained product in Example 1.

EXAMPLE 5

A reaction was carried out in the same manner as in Example 1 except that the following halogen-containing salts were added to the aqueous solution of hypochlorous acid used.

| Halogen-containing salt (mole equivalent) | Yield (%) |
| --- | --- |
| NaBr (2.6) | 95 |
| KBr (2.6) | 97 |
| Et$_4$NBr (2.6) | 96 |
| LiBr (2.6) | 96 |
| NH$_4$Br (2.6) | 95 |

$^1$H-NMR data of obtained product were identical with those of obtained product in Example 1.

EXAMPLE 6

A reaction was carried out in the same manner as in Example 1 except that the following oxidizing agents were used in place of sodium hypochlorite used as the oxidizing agent and that saturated aqueous solution of sodium bicarbonate was used as the solvent:

| Oxidizing agent (mole equivalent) | Yield (%) |
| --- | --- |
| m-Chloroperbenzoic acid (1.1) | 97 |
| Chlorine molecule (1.3) | 95 |
| Bromine molecule (1.1) | 92 |
| Sodium chlorite (1.1) | 90 |
| Sodium bromite (1.1) | 96 |
| Hydrogen peroxide/sodium tungstate (1.1/0.05) | 95 |
| Hydrogen peroxide/tungstic acid (1.1/0.05) | 94 |

EXAMPLE 7

A reaction was carried out in the same manner as in Example 1 with the exception of using the following compounds in place of 4-benzoyloxy-2,6-tetramethylpiperidine-N-oxyl compound as the catalyst (the amount being the same as in Example 1 in terms of mole equivalent).

| Oxyl compound | Yield |
| --- | --- |
| 4-(4-Tert-butylbenzoyloxy)-2,6-tetramethylpiperidine-N-oxyl | 93% |
| 4-Cyano-2,6-tetramethylpiperidine-N-oxyl | 94% |
| 4-Hydroxy-2,6-tetramethylpiperidine-N-oxyl | 95% |
| 4-Methoxy-2,6-tetramethylpiperidine-N-oxyl | 95% |
| 2,6-Tetramethylpiperidine-N-oxyl | 90% |
| 3-Benzoyloxymethyl-2,5-tetramethylpyrrolidine-N-oxyl | 95% |
| 3-Methoxycarbonyl-2,5-tetramethylpyrrolidine-N-oxyl | 95% |
| Di(2,6-tetramethylpiperidine-N-oxyl)-4-yl-1,10-decanoic acid diester | 89% |

EXAMPLE 8

A reaction was carried out in the same manner as in Example 1 with the exception of using the following compounds as the compound (1) (the amount of alcohol used as the raw material being 1.0 mmol).

TABLE 1

| alcohol | product | Yield (%) | $^1$H-NMR (200 MHz, CDCl$_3$, δ ppm) |
| --- | --- | --- | --- |
| Ph-CH(OH)-CH$_3$ | Ph-CO-CH$_3$ | 85 | 2.6(s, 3H), 7.4–7.6(m, 3H), 8.0(d, J=8.1Hz, 2H) |
| MeO-C$_6$H$_4$-CH(OH)-CH$_3$ | MeO-C$_6$H$_4$-CO-CH$_3$ | 72 | 2.5(s, 3H), 3.9(s, 3H), 6.9(d, J=8.1Hz, 2H), 8.0(d, J=8.1Hz, 2H) |
| Me-C$_6$H$_4$-CH(OH)-CH$_3$ | Me-C$_6$H$_4$-CO-CH$_3$ | 87 | 2.4(s, 3H), 2.6(s, 3H), 7.3(d, J=8.1Hz, 2H), 7.9(d, J=8.1Hz, 2H) |
| tBu-C$_6$H$_4$-CH(OH)-CH$_3$ | tBu-C$_6$H$_4$-CO-CH$_3$ | 91 | 1.3(s, 9H), 2.6(s, 3H), 7.5(d, J=8.7Hz, 2H), 7.9(d, J=8.7Hz, 2H) |
| Ph-CH$_2$-CH$_2$-CH(OH)-CH$_3$ | Ph-CH$_2$-CH$_2$-CO-CH$_3$ | 87 | 2.1(s, 3H), 2.7–3.0(m, 4H), 7.1–7.3(m, 5H) |

EXAMPLE 9

There were weighed out an alkyldiol compound (1) (144 mg, 1.00 mmol) and 4-benzoyloxy-2,6-tetramethylpiperidine-N-oxyl compound (3.0 mg, 0.01 mmol). Then, 2 ml of acetone was added to obtain a uniform solution. Added thereto was 1 g of silica gel (product of Merck, grade 9385) and the mixture was vigorously agitated for 5 minutes. The acetone used was distilled off under reduced pressure. The eggplant type flask containing the obtained silica gel was immersed in an ice bath and cooled to 1 to 2° C. Thereto added gradually dropwise was a cooled solution of sodium hypochlorite prepared aside from the above (5 ml of aqueous solution containing 2.4 mmols of active oxygen). After completion of addition, the reaction mixture was stirred at the same temperature for 30 minutes. After completion of stirring, the reaction mixture was filtered. Then, the silica gel remaining on the filter paper was washed with 5 ml of acetone to recover the reaction product and catalyst. Acetone was removed by concentration and the residue was purified by silica gel column chromatography (ethyl acetate/hexane=7/1), whereby lactone compound 2 (132 mg, yield 98%) was obtained. The obtained lactone compound showed the following $^1$H-NMR data.

$^1$H-NMR (200 MHz, CDCl$_3$)

δ ppm: 1.2–2.6(m, 10H), 3.9(d, J=10.8 Hz, 1H), 4.2(dd, J=4.2, 10.8 Hz, 1H)

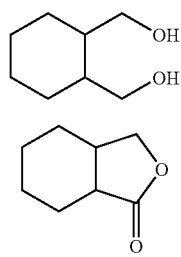

EXAMPLE 10

The same reaction as in Example 1 was conducted except that the following compounds were used in place of the compound (1) with the results shown in Table 2 (the amount of alcohol used as the raw material being 1.0 mmol).

EXAMPLE 11

There were weighed out 1-phenylethanol (122 mg, 1.00 mmol) and 4-benzoyloxy-2,2,6,6-tetramethylpiperidine-N-oxyl compound (3.0 mg, 0.01 mmol). Then, 2 ml of acetone was added to obtain a uniform solution. Added thereto was 500 mg of silica gel (product of Merck, grade 9385) and the mixture was vigorously agitated for 5 minutes. The acetone used was distilled off under reduced pressure. Added thereto was 7% aqueous solution of sodium bicarbonate (5 ml) containing 20 wt % of sodium bromide. Then, the mixture was thoroughly stirred. Two platinum electrodes (1.5×1.0 cm) were applied to the mixture which was then subjected to electrolytic oxidation reaction for 2 hours while being vigorously stirred at room temperature and maintaining the current at 30 mA (quantity of electricity being 2.2 F/mol). After completion of reaction, silica gel was filtered off from the reaction mixture, extraction was effected with 5 ml of acetone and acetone was distilled off. The obtained residue was passed through silica gel column to adsorb it on the column, and elution was performed with a solvent mixture of ethyl acetate/hexane=7/1, giving 116 mg of acetophenone in a yield of 96%.

$^1$H-NMR (200 MHz, CDCl$_3$)

δ ppm: 2.6(s, 3H), 7.4–7.6(m, 3H), 8.0(d, J=8.1 Hz, 2H)

EXAMPLES 12 TO 19

The same reaction as in Example 11 was carried out with the exception of using the compounds shown in Table 3 as silica gel. Table 3 also indicates the yield of the obtained acetophenone.

TABLE 3

| | Silica Gel (Trade name) | Yield (%) |
| --- | --- | --- |
| Example 12 | Wakogel c-200, product of Wako Pure Chemical Ind., Ltd. | 94 |
| Example 13 | Wakogel c-300, product of Wako Pure Chemical Ind., Ltd. | 94 |
| Example 14 | Silica Gel 60, spherical, Product of Kanto Kagaku K.K. | 95 |

TABLE 2

| diol | Product | Yield (%) | $^1$HNMR (200 MHz, CDCl$_3$, δ ppm) |
| --- | --- | --- | --- |
| HO~~~OH | (γ-butyrolactone) | 92 | 1.6–1.7(m, 2H), 2.5(t, J=8.0Hz, 2H), 4.3(t, J=8.8Hz, 2H) |
| HO~~~~OH | (δ-valerolactone) | 87 | 1.8–1.9(m, 4H), 2.5(d, J=6.8Hz, 2H), 4.3(t, J=6.5Hz, 2H) |
| (branched diol with OH) | (alkyl-substituted γ-lactone) | 98 | 0.86(t, J=6.7Hz, 3H), 1.2–1.9(m, 10H), 2.2–2.6(m, 2H), 4.4–4.5(m, 1H) |

TABLE 3-continued

| | Silica Gel (Trade name) | Yield (%) |
|---|---|---|
| Example 15 | Silica Gel 60, spherical, neutral, product of Kanto Kagaku K.K. | 96 |
| Example 16 | Silica Gel 60, spherical, 100 to 200 mesh, product of Kanto Kagaku K.K. | 95 |
| Example 17 | Silica Gel 60, spherical, 40 to 100 mesh, product of Kanto Kagaku K.K. | 95 |
| Example 18 | YMC Gel SIL-60-230/70, product of YMC K.K. | 92 |
| Example 19 | Silica Gel 60, KO70, product of Katayama Gel K.K. | 90 |

EXAMPLES 20 TO 26

The same reaction as in Example 11 was carried out with the exception of changing the electric current and the energizing time as shown in Table 4. Table 4 also indicates the yield of the obtained acetophenone.

TABLE 4

| | electric current (mA) | energizing time (hour) | Yield (%) |
|---|---|---|---|
| Example 20 | 2 | 30 | 90 |
| Example 21 | 5 | 12 | 92 |
| Example 22 | 10 | 6 | 94 |
| Example 23 | 20 | 3 | 96 |
| Example 24 | 40 | 1.5 | 96 |
| Example 25 | 60 | 1 | 88 |
| Example 26 | 120 | 0.5 | 80 |

EXAMPLES 27 TO 35

The same reaction as in Example 11 was carried out with the exception of changing the electrodes as shown in Table 5. Table 5 also indicates the yield of the obtained acetophenone.

TABLE 5

| | anode material | cathode material | Yield (%) |
|---|---|---|---|
| Example 27 | platinum | stainless steel | 93 |
| Example 28 | platinum | carbon | 90 |
| Example 29 | platinum | copper | 92 |
| Example 30 | platinum | lead | 89 |
| Example 31 | platinum | nickel | 87 |
| Example 32 | carbon | carbon | 82 |
| Example 33 | carbon | platinum | 82 |
| Example 34 | stainless steel | platinum | 85 |
| Example 35 | stainless steel | carbon | 80 |

EXAMPLES 36 TO 40

The same electrolytic oxidation reaction as in Example 11 was carried out with the exception of using the reaction solvents as shown in Table 6 in place of the reaction solvent containing a supporting electrolyte (saturated aqueous solution of sodium bicarbonate containing 20 wt. % of sodium bromide). Table 6 also indicates the yield of the obtained acetophenone.

TABLE 6

| | reaction solvent containing a supporting electrolyte | | | |
|---|---|---|---|---|
| | supporting electrolyte | conc. (wt %) | conc. of aqueous solution of sodium bicarbonate (wt %) | yield (%) |
| Example 36 | sodium bromide | 10 | 7 | 94 |
| Example 37 | sodium bromide | 20 | 12 | 89 |
| Example 38 | potassium bromide | 20 | 7 | 93 |
| Example 39 | lithium bromide | 20 | 7 | 90 |
| Example 40 | sodium bromide | 20 | 7 | 82 |

EXAMPLES 41 TO 47

The same electrolytic oxidation reaction as in Example 11 was carried out with the exception of using the catalysts as shown in Table 7 in place of the catalyst (4-benzoyloxy-2,2,6,6-tetramethylpiperidine-N-oxyl compound). Table 7 also indicates the yield of the obtained acetophenone.

TABLE 7

| Example | Catalyst | Yield (%) |
|---|---|---|
| 41 | 4-(4-Tert-butylbenzoyloxy)-2,2,6,6-tetramethylpiperidine-N-oxyl | 93 |
| 42 | 4-Cyano-2,2,6,6-tetramethylpiperidine-N-oxyl | 94 |
| 43 | 4-Methoxy-2,2,6,6-tetramethylpiperidine-N-oxyl | 95 |
| 44 | 2,2,6,6-tetramethylpiperidine-N-oxyl | 90 |
| 45 | 3-Benzoyloxymethyl-2,2,5,5-tetramethylpyrrolidine-N-oxyl | 95 |
| 46 | 3-Methoxycarbonyl-2,2,5,5-tetramethylpyrrolidine-N-oxyl | 95 |
| 47 | Di(2,2,6,6-tetramethylpiperidine-N-oxyl)-4-yl-1,10-decanoic acid diester | 89 |

EXAMPLE 48

An electrolytic oxidation reaction was carried out in the same manner as in Example 11 with the exception of using, as the solvent containing a supporting electrolyte, the aqueous solution of sodium bicarbonate containing the sodium bromide remaining after collecting silica gel by filtration from the reaction mixture resulting from the electrolytic oxidation reaction in Example 11. Thereby the contemplated acetophenone was obtained in a yield of 86%.

EXAMPLES 49 TO 51

An electrolytic oxidation reaction was carried out in the same manner as in Example 11 with the exception of using the starting compounds shown in Table 8 in place of 1-phenylethanol. Table 8 also indicates the obtained reaction products, their yields, and $^1$H-NMR spectrum data.

TABLE 8

| Example | starting compound | product | yield (%) | ¹H-NMR: δ ppm (200 MHz, CDCl₃) |
|---|---|---|---|---|
| 49 | 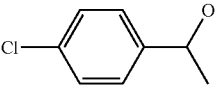 | 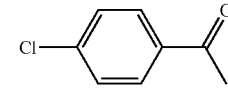 | 90 | 2.60(s, 3H), 7.60(d, J=8.1Hz, 2H) 7.81(d, J=8.1Hz, 2H) |
| 50 | 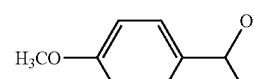 | 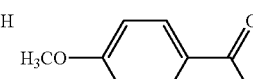 | 70 | 2.51(s, 3H), 3.88(s, 3H), 6.94(d, J=8.1Hz, 2H) 7.95(d, J=8.1Hz, 2H) |
| 51 | 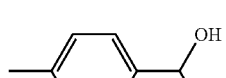 | 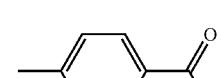 | 85 | 2.40(s, 3H), 2.57(s, 3H), 7.25(d, J=8.1Hz, 2H) 7.85(d, J=8.1Hz, 2H) |

EXAMPLE 52

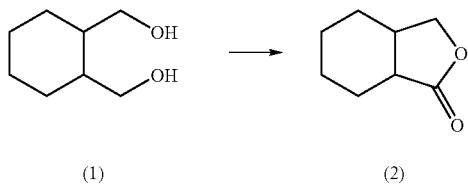

An electrolytic oxidation reaction was carried out in the same manner as in Example 11 with the exception of using 144 mg (1.0 mmol) of 1,2-bis(hydroxymethyl)cyclohexane (1) in place of 122 mg (1.00 mmol) of 1-phenylethanol and conducting the reaction for 4 hours (quantity of electricity being 4.5 F/mol), thereby giving 123 mg (yield 92%) of 8-oxabicyclo[4,3,0]nonane-7-one (2).

¹H-NMR (200 MHz, CDCl₃)

δ ppm: 1.2~2.6(m, 10H), 3.9(d, J=8.8 Hz, 1H), 4.2(dd, J=4.2, 8.0 Hz, 1H)

EXAMPLES 53 TO 55

An electrolytic oxidation reaction was carried out in the same manner as in Example 52 with the exception of using the starting compounds as shown in Table 9 in place of 1,2-bis(hydroxymethyl)cyclohexane (1). Table 9 also indicates the obtained reaction products, their yields, and ¹H-NMR spectrum data.

TABLE 9

| Ex. | starting compound | product | Yield (%) | ¹H-NMR: δ ppm (200 MHz, CDCl₃) |
|---|---|---|---|---|
| 53 | HO~~~OH | (γ-butyrolactone) | 89 | 1.56–1.71(m, 2H), 2.47(t, J=8.0Hz, 2H) 4.33(d, J=8.8Hz, 2H) |
| 54 | HO~~~~OH | (δ-valerolactone) | 82 | 1.84–1.86(m, 4H), 2.54(d, J=6.8Hz, 2H) 4.33(d, J=6.5Hz, 2H) |
| 55 | (diol structure) | (lactone) | 96 | 0.86(t, J=6.7Hz, 3H), 1.26–1.93(m, 10H), 2.21–2.56(m, 2H) 4.40–4.53(m, 1H) |

EXAMPLE 56

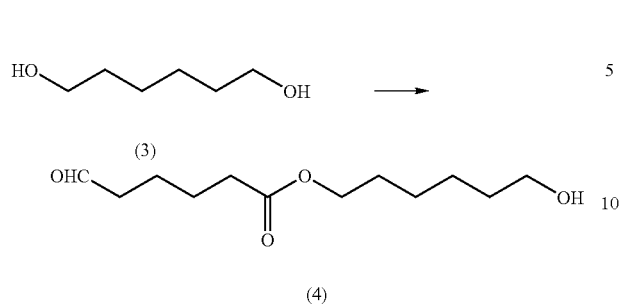

An electrolytic oxidation reaction was carried out in the same manner as in Example 52 with the exception of using 1,6-hexanediol (3) instead of 1,2-bis(hydroxymethyl)cyclohexane (1). Thereby 5-formylpentanoic acid-6'-hydroxyhexyl ester (4) was obtained in a yield of 75%.

EXAMPLE 57

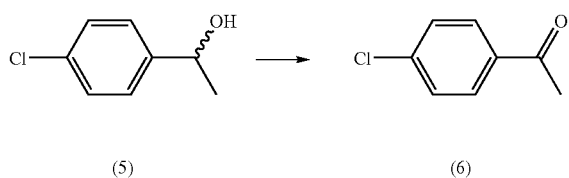

There were weighed out p-chlorophenyl-ethanol (5, racemic compound) (78 mg, 0.05 mmol) and (S)-(−)-3,3,5,5-tetramethyl-4H-dinaphtho[2,1-c:1',2'-e]-azepin-N-oxyl (1.8 mg, 0.05 mmol). Then, 2 ml of acetone was added to obtain a uniform solution. Added thereto was 250 mg of silica gel (product of Merck, grade 9385) and the mixture was vigorously agitated for 5 minutes. The acetone used was distilled off under reduced pressure. Added thereto was 7% aqueous solution of sodium bicarbonate (5 ml) containing 20 wt. % of sodium bromide. Then, the mixture was thoroughly stirred. Two platinum electrodes (1.5×1.0 cm) were applied to the mixture which was then subjected to electrolytic oxidation reaction for 0.68 hour while being vigorously stirred at −15° C. and maintaining the current at 30 mA (quantity of electricity being 2.2 F/mol). After completion of reaction, silica gel was filtered off from the reaction mixture, extraction was effected with 5 ml of acetone and acetone was distilled off. The obtained residue was purified by silica gel column chromatography (ethyl acetate/hexane=7/1), giving p-chloroacetophenone (6) [39 mg, yield 100% based on the starting compound (5a)] and the starting compound (5b) (38 m, recovery percentage 97%, optical purity 83%).

The obtained ketone compound (6) was identical in $^1$H-NMR data with the compound obtained in Example 49. The recovered optically active alcohol compound was identical in $^1$H-NMR data with the racemic compound (5) used as the starting material. The optical purity was obtained by analysis of the mixture under conditions under which the racemic compound can be separated using an optically active HPLC column and by calculation from the area.

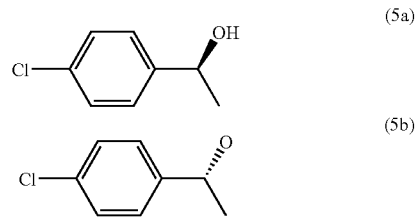

EXAMPLE 58

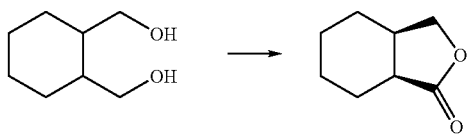

There were weighed out 1,2-bis(hydroxymethyl)cyclohexane (7, meso compound) (144 mg, 1.00 mmol) and (S)-(−)-3,3,5,5-tetramethyl-4H-dinaphtho[2,1-c:1',2'-e]-azepin-N-oxyl (3.0 mg, 1.00 mmol). Then, 2 ml of acetone was added to obtain a uniform solution. Two platinum electrodes (1.5×1.0 cm) were applied to the solution which was then subjected to an electrolytic oxidation reaction for 4 hours while being vigorously stirred at 0° C. and maintaining the current at 30 mA (quantity of electricity being 4.5 F/mol). After completion of reaction, silica gel was filtered off from the reaction mixture, extraction was effected with 5 ml of acetone and acetone was distilled off. The obtained residue was purified by silica gel column chromatography (ethyl acetate/hexane=7/1), giving (1R, 6S)-8-oxabicyclo [4.3.0]nonan-7-one (8) (cis lactone) (122 mg, yield 92%, optical purity 85%).

$^1$H-NMR (200 MHz, CDCl$_3$)

δ ppm: 1.2–2.6(m, 10H), 3.9(d, J=10.8 Hz, 1H), 4.2(dd, J=4.2, 10.8 Hz, 1H)

INDUSTRIAL APPLICABILITY

The present invention can provide a novel process for oxidation of alcohol, the process being capable of producing the contemplated product by a very simple reaction operation in a high yield regardless of the type of alcohol used as the raw material and the process being applicable to all kinds of industrial manufacture without a need for use of an organic solvent which would be likely to adversely affect the environment.

According to the present invention, an oxide higher in oxidizing degree than alcohol such as aldehyde, ketone, lactone, carboxylate, carboxylic acid compounds and the like can be prepared by electrolytically oxdizing in water an alcohol compound which is sparingly soluble in water with high efficiency in a high yield in a manner to overcome the drawbacks of conventional electrolytic oxidation methods.

The invention claimed is:

1. A process for producing an oxide from an alcohol compound, the process comprising the steps of causing silica gel to carry thereon the alcohol compound and an oxidative catalyst selected from the group consisting of N-oxyl compounds and corresponding N-hydroxy compounds, and subjecting the alcohol compound to an electrolytic oxidtion in an aqueous phase, giving an oxide higher in oxidizing degree than the alcohol compound.

2. A process for producing an oxide from an alcohol compound, the process comprising the steps of causing silica gel to carry thereon the alcohol compound and an oxidative catalyst selected from the group consisting of N-oxyl compounds and corresponding N-hydroxy compounds, and subjecting the alcohol compound to an electrolytic oxidation in an aqueous phase in the presence of a supporting electrolyte, giving an oxide higher in oxidizing degree than the alcohol compound.

3. The process according to claim 2, wherein the catalyst for electrolytic oxidation is N-oxyl compound.

4. The process according to claim 1, wherein the alcohol compound is one which is sparingly soluble in water.

5. The process according to claim 2, wherein the alcohol compound is one which is sparingly soluble in water.

6. The process according to claim 1, wherein oxides higher in oxidizing degree than the alcohol are aldehyde, ketone, lactone, carboxylic acid ester, and carboxylic acid compound.

7. The process according to claim 2, wherein oxides higher in oxidizing degree than the alcohol are aldehyde, ketone, lactone, carboxylic acid ester, and carboxylic acid compound.

8. The process according to claim 4, wherein oxides higher in oxidizing degree than the alcohol are aldehyde, ketone, lactone, carboxylic acid ester, and carboxylic acid compound.

9. The process according to claim 5, wherein oxides higher in oxidizing degree than the alcohol are aldehyde, ketone, lactone, carboxylic acid ester, and carboxylic acid compound.

10. The process according to claim 3, wherein oxides higher in oxidizing degree than the alcohol are aldehyde, ketone, lactone, carboxylic acid ester, and carboxylic acid compound.

* * * * *